United States Patent [19]

Lürssen et al.

[11] 4,150,967

[45] Apr. 24, 1979

[54] AGENTS FOR REGULATING PLANT GROWTH

[75] Inventors: Klaus Lürssen, Berg. Gladbach; Ulrich Holtschmidt; Günter Schwarzmann, both of Essen, all of Fed. Rep. of Germany

[73] Assignee: Bayer Aktiengesellschaft, Leverkusen, Fed. Rep. of Germany

[21] Appl. No.: 872,969

[22] Filed: Jan. 27, 1978

[30] Foreign Application Priority Data

Feb. 17, 1977 [DE] Fed. Rep. of Germany ....... 2706839

[51] Int. Cl.$^2$ .......................... A01N 5/00; A01N 9/22
[52] U.S. Cl. ............................................ 71/92; 71/76
[58] Field of Search ...................................... 71/92, 76

[56] References Cited

U.S. PATENT DOCUMENTS 2,710,870  6/1955  Lawson ................................... 71/92

FOREIGN PATENT DOCUMENTS 42-9473  5/1967  Japan.

*Primary Examiner*—Catherine L. Mills
*Attorney, Agent, or Firm*—Sprung, Felfe, Horn, Lynch & Kramer

[57] ABSTRACT

Novel quaternary imidazolium compounds and the use of quaternary imidazolium compounds as plant growth regulants and the preparation of certain quaternary imidazolium derivatives.

39 Claims, No Drawings

AGENTS FOR REGULATING PLANT GROWTH

BACKGROUND OF THE INVENTION

1. Field of the Invention

The present invention relates to the use, as plant growth regulators, of certain quaternary imidazolium compounds, some of which are known.

2. Discussion of the Prior Art

It has already been disclosed in German Offenlegungsschriften Nos. 2,508,420 and 2,510,525 that certain quaternary imidazolium compounds possess a microbicidal activity.

Furthermore, it is known from R. Wegler "Chemie der Pflanzenschutz- und Schädlingsbekämpfugsmittel" ("Chemistry of Agetns for Protecting Plants and for Combating Pests" Volumn 2, page 265) that succinic acid 2,2-dimethylhydrazide possesses plant-growth-regulating properties. However, the action of this substance is not always satisfactory, especially when applied at low application rates.

In addition, it has also been disclosed in U.S. Pat. No. 3,156,554 that certain 2-halogeno-ethyl-trialkylammonium halides have plant growth-regulating properties. Thus, plant growth can be influenced, for example, with the aid of (2-chloroethyl)-trimethyl-ammonium chloride. However, the activity of this substance is not always sufficient, especially at low application rates.

SUMMARY OF THE INVENTION

It has now been found that the quaternary imidazolium compounds of the general formula

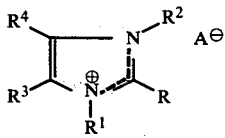

(I), in which
R represents hydrogen or alkyl with 1 to 4 carbon atoms,
$R^1$ represents alkyl,
$R^2$ represents hydrogen, alkyl or optionally substituted benzyl,
$R^3$ represents hydrogen or methyl,
$R^4$ represents hydrogen or methyl and
$A^\ominus$ represents an equivalent of an anion of a non-phytotoxic acid,
have powerful plant growth-regulating properties.

Accordingly, the present invention provides a method of regulating the growth of plants, which comprises applying to the plants, or to a habitat thereof, a compound of the formula (I) alone or in admixture with a diluent or carrier.

The invention also provides plants, the growth of which has been regulated by their being grown in areas in which immediately prior to and/or during the time of the growing a compound of the formula (I) has been applied alone or in admixture with a diluent or carrier.

Preferably, in the formula (I), R represents hydrogen or unbranched alkyl with 1 to 3 carbon atoms, $R^1$ represents alkyl with 8 to 16 carbon atoms, $R^2$ represents hydrogen, alkyl with 1 to 12 carbon atoms or benzyl which is optionally monosubstituted or polysubstituted in the phenyl part by halogen, and $A^{63}$ represents halide (for example chloride, bromide or iodide) or alkylsulphate (for example methylsulphate or ethylsulphate).

Surprisingly, the quaternary imidazolium compounds which can be used according to the invention exhibit a better plant growth-regulating activity than succinic acid 2,2-dimethyl-hydrazide, which is known from the state of the art, and (2-chloroethyl)-trimethylammonium chloride, which is also known, and which are substances of the same type of action and having an activity which is acknowledged as good. The substances which can be used according to the invention thus represent a valuable enrichment of the art.

The formula (I) provides a general definition of the quaternary imidazolium compounds which can be used according to the invention. The above way of drawing the formula was chosen in order to show that a more or less highly delocalised $\pi$-electron system is present in the five-membered ring of the imidazolium cation. However, it is also possible to represent the electron distribution in the imidazolium cations by the following canonical structures with fixed bonds:

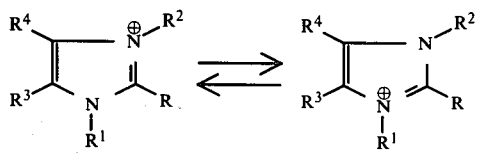

The actual $\pi$-electron distribution in the five-membered ring is only approximately illustrated by each of these two canonical structures. In many cases a single structural formula with fixed double bonds is not sufficient to show the actual state of bonding precisely. For this reason, the compounds which can be used according to the invention are in each case represented in this specification in a simplified manner by a formula in which the distribution of the $\pi$-electrons in the five-membered ring of the cation is indicated by a dotted line (as in formula (I)).

Individual examples of the active compounds which can be used according to the invention are: 1-octyl-3-methyl-imidazolium bromide, 1-octyl-3-methyl-imidazolium iodide, 1-octyl-3-methyl-imidazolium methosulphate, 1-dodecyl-3-ethyl-imidazolium bromide, 1-octyl-3-ethyl-imidazolium bromide, 1-octyl-3-ethyl-imidazolium iodide, 1-octyl-3,4,5-trimethyl-imidazolium bromide, 1-octyl-2,3-dimethyl-imidazolium bromide, 1-octyl-2,3-dimethyl-imidazolium iodide, 1-octyl-2,3-dimethyl-imidazolium methosulphate, 1-dodecyl-3-propyl-imidazolium bromide, 1-dodecyl-3-propyl-imidazolium iodide, 1-dodecyl-3-propyl-imidazolium chloride, 1-dodecyl-2-methyl-imidazolium bromide, 1,3-di-dodecyl-2-ethyl-imidazolium bromide, 1-hexadecyl-3-ethyl-imidazolium bromide, 1-hexadecyl-3-ethyl-imidazolium chloride, 1-hexadecyl-3-methyl-imidazolium iodide, 1-hexadecyl-3-methyl-imidazolium methosulphate, 1-octyl-3-(4-chlorobenzyl)-imidazolium chloride, 1-octyl-3-(4-chlorobenzyl)-imidazolium bromide, 1-octyl-3-(3,4-dichlorobenzyl)-imidazolium chloride, 1-octyl-3-(3,4-dichlorobenzyl)-imidazolium bromide, 1,2,4,5-tetramethyl-3-octyl-imidazolium bromide and 1,2,4,5-tetramethyl-3-octyl-imidazolium iodide.

Some of the quaternary imidazolium compounds of the formula (I) which can be used according to the invention are known (compare German Offenlegungsschriften (German Published Specifications Nos.)

2,508,420 and 2,510,525). However, their use for regulating plant growth has not been described in the literature.

Certain of the quaternary imidazolium compounds which can be used according to the invention have not hitherto been described in the literature; however, they can be prepared in a simple manner by known methods. For example, they are obtained by reacting imidazoles of the general formula

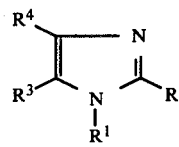

(II), in which

R, $R^1$, $R^3$ and $R^4$ have the meanings stated above, with compounds of the general formula $$R^2—X \qquad (III),$$

in which $R^2$ has the meaning stated above and

X represents halogen, in the presence of a diluent at temperatures between 50° C. and 180° C., preferably between 80° C. and 150° C.

Useful diluents are all the inert polar organic solvents, especially the lower alcohols.

In carrying out the process, at least 1 mole of a compound of the formula (III) is generally employed per mole of an imidazole of the formula (II). The reaction products are isolated by methods which are generally customary. In general, the procedure is to remove the solvent and excess compound of the formula (III) after the reaction has ended, and to wash the reaction product, which thereby remains, with an inert organic solvent and then to dry it.

The anion in the compounds prepared in this manner can be varied by customary methods, for example with the aid of ion exchangers.

Those compounds of the formula (I) in which $A^\ominus$ represents alkyl-sulphate can be prepared by alkylating an imidazole of the formula (II) with the appropriate dialkyl sulphates customary methods.

Both the imidazoles of the formula (II) and the compounds of the formula (III) are known or can be prepared by known processes. See German Offenlegungsschrift No. 2,442,706, the disclosure of which is hereby incorporated herein by reference.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favourably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds according to the instant invention can be utilized, if desired, in the form of the usual formulation or compositions with conventional inert (i.e., plant compatible) diluents or extenders, i.e. diluents, carriers or extenders of the type usable in conventional plant growth formulations or compositions, e.g. conventional dispersible carrier vehicles such as gases, solutions, emulsions, wettable powders, suspensions, powder dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional dispersible liquid diluent carriers and/or dispersible solid carriers optionally with the use of carrier vehicle assistants, e.g., conventional surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons (dichlorodifluoromethane or trichlorofluoromethane) as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.), as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially other plant protection agents, such as other insecticides, acaricides, fungicides, bactericides, rodenticides and fertilizers, if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between 0.0000001-100, preferably 0.01-10% by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of active compound which is effective for the purpose in question and which is generally between about 0.0001–95%, and preferably 0.01–95%, by weight of the mixture, preferably 0.1 to 95%, more preferably 0.5 to 90 weight percent.

The amount of active compound used can vary within a fairly wide range. It depends essentially on the nature of the desired effect. In general, the amounts used are from 0.01 to 50 kg, especially 0.05 to 10 kg of active compound per hectare.

It will be seen that the usual methods of providing a harvested crop may be improved by the present invention.

The plant growth regulating activity of the compounds of this invention is illustrated by the following biotest Examples.

In these Examples, the compounds according to the present invention are each identified by the number (given in brackets) of the corresponding preparative Example, which will be found later in this specification.

The known comparison compounds are identified as follows:

(A) = HOOC-CH$_2$CH$_2$-CO-NH-N(CH$_3$)$_2$
(B) = Cl—CH$_2$CH$_2$—N$^\oplus$(CH$_3$)$_3$Cl $^\ominus$

EXAMPLE A

Inhibition of growth/wheat

Solvent: 10 parts by weight of methanol
Emulsifier: 2 parts by weight of polyoxyethylene sorbitian monolaurate To prepare a suitable preparation of active compound, 1 part by weight of active compound was mixed with the stated amount of solvent and emulsifier and the mixture was made up to the desired concentration with water.

Young wheat plants, 5–8 cm high, were sprayed with the preparation of active compound until dripping wet. After 14 days, the additional growth was measured and the inhibition of growth in % of the additional growth of the control plants was calculated. 100% meant that growth had stopped and 0% denoted a growth corresponding to that of the control plants.

The active compounds, active compound concentrations and results can be seen from the table which follows:

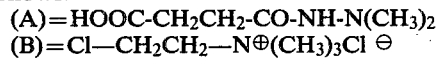
Table A

| Active compound | Active compound concentration in % | Inhibition of growth in % |
|---|---|---|
| — (control) | — | 0 |
| (A) | 0.05 | 0 |
| (19) | 0.05 | 45 |
| (20) | 0.05 | 25 |
| (22) | 0.05 | 25 |
| (24) | 0.05 | 25 |
| (27) | 0.05 | 25 |
| (28) | 0.05 | 25 |

EXAMPLE B

Inhibition of growth/soya beans

Solvent: 10 parts by weight of methanol
Emulsifier: 2 parts by weight of polyoxyethylene sorbitan monolaurate To prepare a suitable preparation of active compound, 1 part by weight of active compound was mixed with the stated amounts of solvent and emulsifier and the mixture was made up to the desired concentration with water.

Young soya bean plants, at the stage in which the first secondary leaves had unfolded, were sprayed with the preparation of active compounds until dripping wet. After 2 weeks, the additional growth was measured and the inhibition of growth in % of the additional growth of the control plants was calculated. 0% denoted growth corresponding to that of the control plants.

The active compounds, concentrations of the active compounds and results can be seen from the table which follows:

Table B

| Active compound | Active compound concentration in % | Inhibition of growth in % |
|---|---|---|
| — (control) | — | 0 |
| (B) | 0.05 | 0 |
| (1) | 0.05 | 55 |
| (2) | 0.05 | 55 |
| (3) | 0.05 | 55 |
| (5) | 0.05 | 55 |
| (6) | 0.05 | 55 |
| (7) | 0.05 | 35 |
| (8) | 0.05 | 55 |
| (12) | 0.05 | 55 |
| (14) | 0.05 | 35 |
| (16) | 0.05 | 55 |
| (17) | 0.05 | 35 |
| (18) | 0.05 | 30 |
| (19) | 0.05 | 55 |
| (20) | 0.05 | 45 |
| (22) | 0.05 | 50 |
| (30) | 0.05 | 80 |
| (25) | 0.05 | 55 |

EXAMPLE C

Inhibition of the growth of side shoots of tobacco

Solvent: 10 parts by weight of methanol
Emulsifier: 2 parts by weight of polyoxyethylene sorbitan monolaurate To prepare a suitable preparation of active compound, 1 part by weight of active compound was mixed with the stated amounts of solvent and emulsifier and the mixture was made up to the desired concentration with water.

The shoot tips of about 50 cm high tobacco plants were broken off. On the following day, the plants were sprayed with the preparations of active compound until dripping wet. After 3 weeks, the side shoots which had formed during this time were broken off. All the side shoots of one treatment were weighed. The weight of the side shoots of the treated plants was compared with the weight of the side shoots of the untreated control plants. 100% inhibition denoted the absence of side shoots and 0% denoted a growth of side shoots which corresponded to that of the control plants.

The active compounds, the concentrations of the active compounds and results can be seen from the table which follows:

Table C

Inhibition of growth of side shoots of tobacco

| Active compound | Active compound concentration in % | Inhibition of growth in % |
|---|---|---|
| (2) | 0.2 | 40 |
| (3) | 0.2 | 22 |
| (20) | 0.2 | 57 |
| (30) | 0.2 | 23 |

EXAMPLE D

Influence on growth/cotton

Solvent: 10 parts by weight of methanol
Emulsifier: 2 parts by weight of polyoxyethylene sorbitan monolaurate To prepare a suitable preparation of active compound, 1 part by weight of active compound was mixed with the stated amount of solvent and emulsifier and the mixture was made up to the desired concentration with water.

Young cotton plants in the 4-leaf stage were sprayed with the preparations of active compound until dripping wet. After 3 weeks, the additional growth was measured and the influence on growth in % of the additional growth of the control plants was calculated. 0% denoted growth corresponding to that of the control plants.

Positive values characterised promotion of growth compared to the control plants whilst negative values correspondingly indicated an inhibition of growth.

The active compounds, concentrations of the active compounds and results can be seen from the table which follows:

Table D

Influence on growth/cotton

| Active compound | Active compound concentration in % | Influence on growth in % |
|---|---|---|
| (1) | 0.05 | + 25*) |
| (2) | 0.05 | − 80*) |
| (3) | 0.05 | − 100*) |
| (4) | 0.05 | − 80*) |
| (5) | 0.05 | − 80*) |
| (6) | 0.05 | − 80*) |
| (7) | 0.05 | + 25 |
| (8) | 0.05 | + 25*) |
| (9) | 0.05 | + 25 |
|     | 0.2  | −*) |
| (10) | 0.05 | + 25*) |
| (11) | 0.05 | − 100*) |
| (12) | 0.05 | − 80*) |
| (13) | 0.05 | − 25*) |
| (14) | 0.05 | + 25 |
| (15) | 0.05 | − 80 |
| (16) | 0.05 | − 100*) |
| (17) | 0.05 | − 80 |
| (18) | 0.05 | + 25*) |
| (19) | 0.05 | − 80*) |
| (20) | 0.05 | − 80*) |
| (21) | 0.05 | + 25 |
| (22) | 0.05 | + 25*) |
| (23) | 0.05 | − 30 |
| (30) | 0.05 | − 80*) |
| (25) | 0.05 | − 100 |
| (26) | 0.05 | + 25 |
| (27) | 0.05 | + 25 |
| (28) | 0.05 | + 25 |
| (29) | 0.05 | + 25 |

*)The sprayed leaves dropped off.

Preparative Examples

EXAMPLE 1

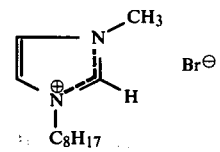

(1A)

1 mole of 1-methylimidazole was dissolved in 400 ml of ethanol and 1.2 moles of n-octyl bromide were added. The mixture was then heated to the boiling point for 5 hours. Thereafter, ethanol and excess n-octyl bromide were removed. The residue was purified in ether. In this manner, 250 g of 1-n-octyl-3-methyl-imidazolium bromide were obtained.

Elementary analysis for $C_{12}H_{23}N_2Br$:

| calculated | found |
|---|---|
| C 52.3% | C 51.4% |
| H 8.4% | H 8.9% |
| N 10.2% | N 10.2% |
| Br 29.1% | Br 30.0% |

The compounds listed in the table which follows were prepared in an analogous manner:

Table 1

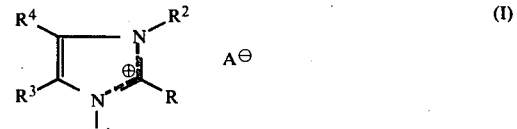

(I)

| Example No. | R | $R^1$ | $R^2$ | $R^3$ | $R^4$ | A | Flowing Point (° C.) |
|---|---|---|---|---|---|---|---|
| 2 | H | $C_{12}H_{25}$ | $C_2H_5$ | H | H | Br | decomposition |
| 3 | H | $C_8H_{17}$ | $C_2H_5$ | H | H | Br | decomposition |
| 4 | $CH_3$ | $C_8H_{17}$ | $CH_3$ | H | H | Br | ≈37 |
| 5 | H | $C_{12}H_{25}$ | $C_3H_7$ | H | H | Br | decomposition |
| 6 | H | $C_8H_{17}$ | $C_3H_7$ | H | H | Br | decomposition |
| 7 | $CH_3$ | $C_{12}H_{25}$ | H | H | H | Br | 54 |
| 8 | $CH_3$ | $C_{12}H_{25}$ | $CH_3$ | H | H | Br | 80 |
| 9 | $CH_3$ | $C_{16}H_{33}$ | $CH_3$ | H | H | Br | 97 |
| 10 | $C_2H_5$ | $C_{12}H_{25}$ | $C_{12}H_{25}$ | H | H | Br | 56 |
| 11 | $C_2H_5$ | $C_8H_{17}$ | $C_8H_{17}$ | H | H | Br | decomposition |

Table 1-continued

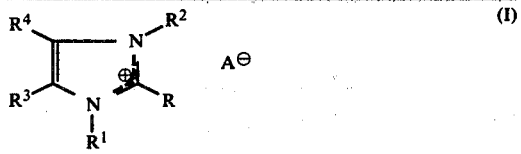

| Example No. | R | R¹ | R² | R³ | R⁴ | A | Flowing Point (°C.) |
|---|---|---|---|---|---|---|---|
| 12 | H | $C_{16}H_{33}$ | $C_3H_7$ | H | H | Br | 28 |
| 13 | $C_2H_5$ | $C_{16}H_{33}$ | $C_8H_{17}$ | H | H | Br | 30 |
| 14 | H | $C_{16}H_{33}$ | $C_8H_{17}$ | H | H | Br | decomposition |
| 15 | H | $C_{16}H_{33}$ | $C_3H_7$ | H | H | Cl | decomposition |
| 16 | H | $C_{16}H_{33}$ | $C_2H_5$ | H | H | Cl | decomposition |
| 17 | $CH_3$ | $C_{12}H_{25}$ | $C_{12}H_{25}$ | H | H | Br | 100 decomposition |
| 18 | $C_3H_7$ | $C_{16}H_{33}$ | $C_8H_{17}$ | H | H | Br | 73–75 |
| 19 | $CH_3$ | $C_8H_{17}$ | $C_8H_{17}$ | H | H | Br | ≈30 |
| 20 | $CH_3$ | $C_{12}H_{25}$ | $C_8H_{17}$ | H | H | Br | ≈25 |
| 21 | $CH_3$ | $C_{16}H_{33}$ | $C_{12}H_{25}$ | H | H | Br | 75 |
| 22 | H | $C_8H_{17}$ | $C_8H_{17}$ | H | H | Br | ≈7 |
| 23 | H | $C_{12}H_{25}$ | $C_{12}H_{25}$ | H | H | Br | 83 |
| 24 | H | $C_{12}H_{25}$ | $C_8H_{17}$ | H | H | Br | 73 |
| 25 | H | $C_8H_{17}$ | $-CH_2-\phi-Cl$ | H | H | Cl | 107 |
| 26 | H | $C_8C_{17}$ | $-CH_2-\phi(Cl)-Cl$ | H | H | Cl | 130 |
| 27 | H | $C_{12}H_{25}$ | $-CH_2-\phi-Cl$ | H | H | Cl | 75–76 |
| 28 | H | $C_{12}H_{25}$ | $-CH_2-\phi(Cl)-Cl$ | H | H | Cl | 116–117 |
| 29 | H | $C_{16}H_{33}$ | $-CH_2-\phi-Cl$ | H | H | Cl | 96 |
| 30 | $CH_3$ | $CH_3$ | $C_8H_{17}$ | $CH_3$ | $CH_3$ | Br | 60 |

What we claimed is:

1. A method of regulating the growth of plants, which comprises applying to the plants, or to a habitat thereof, a quaternary imidazolium compound of the general formula

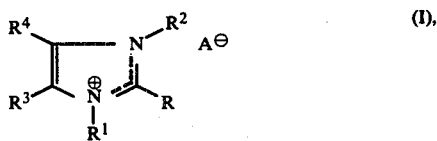

in which
R represents hydrogen or unbranched alkyl with 1 to 3 carbon atoms,
R¹ represents alkyl with 8 to 16 carbon atoms,
R² represents hydrogen, alkyl with 1 to 12 carbon atoms or optionally substituted benzyl, where the substituent is halogen,
R³ represents hydrogen or methyl,
R⁴ represents hydrogen or methyl, and
A⊖ represents an equivalent of a halide or alkyl sulphate anion, alone or in admixture with a diluent or carrier.

2. A method according to claim 1 in which a compound of the formula (I) is applied, in which R represents hydrogen or unbranched alkyl with 1 to 3 carbon atoms, R¹ represents alkyl with 8 to 16 carbon atoms, R² represents hydrogen, alkyl with 1 to 12 carbon atoms or benzyl which is optionally monosubstituted or polysubstituted in the phenyl part by halogen, and A⊖ represents halide or alkylsulphate.

3. A method according to claim 1 wherein the compound of the formula (I) is applied to an area of plant cultivation in an amount of 0.01 to 50 kg per hectare.

4. A method according to claim 3 wherein said compound is applied at a rate of 0.05 to 10 kg per hectare.

5. A method according to claim 1 wherein said compound has the formula

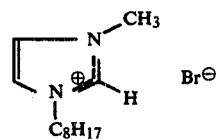

6. A method according to claim 1 wherein in said compound R is hydrogen, R¹ is alkyl of the formula $C_{12}H_{25}$, R² is alkyl of the formula $C_2H_5$, R³ and R⁴ are hydrogen and A is bromine.

7. A method according to claim 1 wherein in said compound R is hydrogen, R¹ is alkyl of the formula $C_8H_{17}$, R² is alkyl of the formula $C_2H_5$, R³ and R⁴ are hydrogen and A is bromine.

8. A method according to claim 1 wherein in said compound R is methyl, R¹ is alkyl of the formula $C_8H_{17}$, R² is methyl, R³ and R⁴ are hydrogen and A is bromine.

9. A method according to claim 1 wherein in said compound R is hydrogen, R¹ is alkyl of the formula $C_{12}H_{25}$, R² is alkyl of the formula $C_3H_7$, R³ and R⁴ are hydrogen and A is bromine.

10. A method according to claim 1 wherein in said compound R is hydrogen, R¹ is alkyl of the formula $C_8H_{17}$, $R^2$ is alkyl of the formula $C_3H_7$, $R^3$ and $R^4$ are hydrogen and A is bromine.

11. A method according to claim 1 wherein in said compound R is methyl, $R^1$ is alkyl of the formula $C_{12}H_{25}$, $R^2$ is hydrogen, $R^3$ and $R^4$ are hydrogen and A is bromine.

12. A method according to claim 1 wherein in said compound R is methyl, $R^1$ is alkyl of the formula $C_{12}H_{25}$, $R^2$ methyl, $R^3$ and $R^4$ ar hydrogen and A is bromine.

13. A method according to claim 1 wherein in said compound R is methyl, $R^1$ alkyl of the formula $C_{16}H_{33}$, $R^2$ is methyl, $R^3$ and $R^4$ are hydrogen and A is bromine.

14. A method according to claim 1 wherein in said compound R is alkyl of the formula $C_2H_5$, $R^1$ is alkyl of the formula $C_{12}H_{25}$, $R^2$ is alkyl of the formula $C_{12}H_{25}$, $R^3$ and $R^4$ are hydrogen and A is bromine.

15. A method according to claim 1 wherein in said compound R is alkyl of the formula $C_2H_5$, $R^1$ is alkyl of the formula $C_8H_{17}$, $R^2$ is alkyl of the formula $C_8H_{17}$, $R^3$ and $R^4$ are hydrogen and A is bromine.

16. A method according to claim 1 wherein in said compound R is hydrogen, $R^1$ is alkyl of the formula $C_{16}H_{33}$, $R^2$ is alkyl of the formula $C_3H_7$, $R^3$ and $R^4$ are hydrogen and A is bromine.

17. A method according to claim 1 wherein in said compound R is alkyl of the formula $C_2H_5$, $R^1$ is alkyl of the formula $C_{16}H_{33}$, $R^2$ is alkyl of the formula $C_8H_{17}$, $R^3$ and $R^4$ are hydrogen and A is bromine.

18. A method according to claim 1 wherein in said compound R is hydrogen, $R^1$ alkyl of the formula $C_{16}H_{33}$, $R^2$ is alkyl of the formula $C_8H_{17}$, $R^3$ and $R^4$ are hydrogen and A is bromine.

19. A method according to claim 1 wherein in said compound R is hydrogen, $R^1$ is alkyl of the formula $C_{16}H_{33}$, $R^2$ is alkyl of the formula $C_3H_7$, $R^3$ and $R^4$ are hydrogen and A is chlorine.

20. A method according to claim 1 wherein in said compound R is hydrogen, $R^1$ is alkyl of the formula $C_{16}H_{33}$, $R^2$ is alkyl of the formula $C_2H_5$, $R^3$ and $R^4$ are hydrogen and A is chlorine.

21. A method according to claim 1 wherein in said compound R is methyl, $R^1$ is alkyl of the formula $C_{12}H_{25}$, $R^2$ is alkyl of the formula $C_{12}H_{25}$, $R^3$ and $R^4$ are hydrogen and A is bromine.

22. A method according to claim 1 wherein in said compound R is alkyl of the formula $C_3H_{17}$, $R^1$ is alkyl of the formula $C_{16}H_{33}$, $R^2$ is alkyl of the formula $C_8H_{17}$, $R^3$ and $R^4$ are hydrogen and A is bromine.

23. A method according to claim 1 wherein in said compound R is methyl, $R^1$ is alkyl of the formula $C_8H_{17}$, $R^2$ is alkyl of the formula $C_8H_{17}$, $R^3$ and $R^4$ are hydrogen and A is bromine.

24. A method according to claim 1 wherein in said compound R is methyl, $R^1$ is alky of the formula $C_{12}H_{25}$, $R^2$ is alkyl of the formula $C_8H_{17}$, $R^3$ and $R^4$ are hydrogen and A is bromine.

25. A method according to claim 1 wherein in said compound R is methyl, $R^1$ alkyl of the formula $C_{16}H_{33}$, $R^2$ is alkyl of the formula $C_{12}H_{25}$, $R^3$ and $R^4$ are hydrogen and A is bromine.

26. A method according to claim 1 wherein in said compound R is hydrogen, $R^1$ is alkyl of the formul $C_8H_{17}$, $R^2$ is alkyl of the formula $C_8H_{17}$, $R^3$ and $R^4$ are hydrogen and A is bromine.

27. A method according to claim 1 wherein in said compound R is hydrogen, $R^1$ is alkyl of the formula $C_{12}H_{25}$, $R^2$ is alkyl of the formula $C_{12}H_{25}$, $R^3$ and $R^4$ are hydrogen and A is bromine.

28. A method according to claim 1 wherein in said compound R is hydrogen, $R^1$ is alkyl of the formula $C_{12}H_{25}$, $R^2$ is alkyl of the formula $C_8H_{17}$, $R^3$ and $R^4$ are hydrogen and A is bromine.

29. A method according to claim 1 wherein in said compound R is hydrogen, $R^1$ is alkyl of the formula $C_8H_{17}$, $R^2$ has the formula

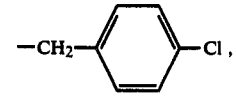

$R^3$ and $R^4$ are hydrogen and A is chlorine.

30. A method according to claim 1 wherein in said compound R is hydrogen, $R^1$ is alkyl of the formula $C_8H_{17}$, $R^2$ has the formula

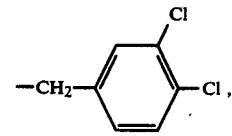

$R^3$ and $R^4$ are hydrogen and A is chlorine.

31. A method according to claim 1 wherein in said compound R is hydrogen, $R^1$ is alkyl of the formula $C_{12}H_{25}$, $R^2$ has the formula

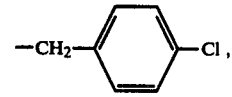

$R^3$ and $R^4$ are hydrogen and A is chlorine.

32. A method according to claim 1 wherein in said compound R is hydrogen, $R^1$ is alkyl of the formula $C_{12}H_{25}$, $R^2$ has the formula

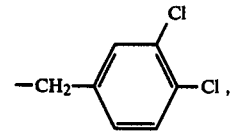

$R^3$ and $R^4$ are hydrogen and A is chlorine.

33. A method according claim 1 wherein in said compound R is hydrogen, $R^1$ is alkyl of the formula $C_{16}H_{33}$, $R^2$ has the formula

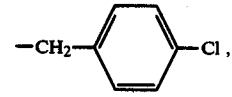

$R^3$ and $R^4$ are hydrogen and A is chlorine.

34. A method according to claim 1 wherein in said compound R, $R^1$, $R^3$ and $R^4$ are methyl, $R^2$ is alkyl of the formula $C_8H_{17}$ and A is bromine.

35. A method according to claim 1 wherein the plant is wheat.

36. A method according to claim 1 wherein the plant is soy bean.

37. A method according to claim 1 wherein the plant is tobacco.

38. A method according to claim 1 wherein the plant is cotton.

39. A method according to claim 1, wherein $R^2$ is alkyl with 1-12 carbon atoms or benzyl or mono or polysubstituted benzyl where the substituent is halogen.

* * * * *

UNITED STATES PATENT AND TRADEMARK OFFICE
CERTIFICATE OF CORRECTION

PATENT NO. : 4,150,967
DATED : April 24, 1979
INVENTOR(S) :

It is certified that error appears in the above—identified patent and that said Letters Patent are hereby corrected as shown below:

Column 1, line 68, "$A^{63}$" should read -- $A^{\ominus}$ --.

Column 13, line 9, claim 12, "ar" should read -- are --.

Signed and Sealed this

Fourth Day of September 1979

[SEAL]

Attest:

LUTRELLE F. PARKER
*Attesting Officer*   *Acting Commissioner of Patents and Trademarks*